United States Patent [19]

Ruppert et al.

[11] Patent Number: 5,218,145
[45] Date of Patent: Jun. 8, 1993

[54] METHOD FOR MAKING ISOBUTYRIC ACID

[75] Inventors: Wolfgang Ruppert, Bickenbach; Hermann-Josef Siegert, Seeheim-Jugenheim, both of Fed. Rep. of Germany

[73] Assignee: Röhm GmbH, Darmstadt, Fed. Rep. of Germany

[21] Appl. No.: 260,032

[22] Filed: Oct. 20, 1988

[30] Foreign Application Priority Data

Jan. 11, 1988 [DE] Fed. Rep. of Germany ....... 3800466

[51] Int. Cl.$^5$ .............................................. C07C 51/14
[52] U.S. Cl. ..................................... 562/521; 560/233
[58] Field of Search ......................... 562/521; 560/233

[56] References Cited

U.S. PATENT DOCUMENTS

| 2,154,795 | 4/1939 | Westenberg | 196/10 |
| 4,452,999 | 6/1984 | Besecke et al. | 560/233 |
| 4,590,293 | 5/1986 | Pascoe | 560/233 |
| 4,647,696 | 3/1987 | Besecke et al. | 562/606 |
| 4,791,227 | 12/1988 | Neumann et al. | 562/521 |

FOREIGN PATENT DOCUMENTS 0031886 7/1981 European Pat. Off. .
0076367 4/1983 European Pat. Off. .
0091604 10/1983 European Pat. Off. .

OTHER PUBLICATIONS

New Synthesis with Carbon Monoxide, edited by J. Falbe, Springer-Verlag, Berlin, 1980 pp. 372–374.

*Primary Examiner*—José G. Dees
*Assistant Examiner*—Samuel Barts

[57] ABSTRACT

In the manufacture of isobutyric acid or its precursors or esters by the Koch synthesis from propylene, carbon monoxide, and, optionally, water or an alcohol in liquid hydrogen fluoride, the reaction mixture is maintained at a constant reaction temperature in a heat exchanger using an addition product of at least two of the aforementioned materials, preferably isopropanol, as a coolant.

7 Claims, No Drawings

METHOD FOR MAKING ISOBUTYRIC ACID

The present invention pertains to an improved method for making isobutyric acid or related compounds by the Koch synthesis from about stoichiometric amounts of propylene and carbon monoxide, in liquid hydrogen fluoride as a Koch catalyst, suitably in the presence of water or an alcohol, and relates particularly to such a method wherein heat is exchanged between the Koch reaction mixture and a coolant comprising an additional product of at least two of the reagents.

The Prior Art

The reactions involved in the Koch synthesis run rapidly and with considerable evolution of heat if they are carried out under high pressure and with a high degree of backmixing. For this reason an intensive cooling of the reaction mixture with a liquid coolant for maintenance of a uniform reaction temperature is, under just such conditions, indispensable, particularly in a continuously operated process. A method for making isobutyric acid or its lower alkyl esters which can be performed continuously in the aforementioned manner is described in EP-B 31,886 corresponding to U.S. Pat. No. 4,452,999. Isobutyric acid fluoride can be prepared in a similar fashion according to EP-B 91,604. The reaction temperatures are 100° C. to 140° C. in the first mentioned method and 40° C. to 90° C. in the latter. Since the reactions are exothermic, the reaction temperature must be maintained at a constant value by cooling.

Problem and Solution

For maintaining a uniform temperature, excess heat of reaction is withdrawn from the reaction mixture in a heat exchanger. To effect this, a liquid coolant is flushed through the heat exchanger. Water is the coolant most used technically.

In this situation, when choosing the coolant it is advisable from safety considerations to keep in mind the high content of hydrogen fluoride in the reaction mixture. Even if materials which are resistant to the reaction mixture under the reaction conditions are known from EP-B 76,367, the danger of a leak in the heat exchange surface between the reaction mixture and the coolant cannot be ignored. The object of the invention is to preclude the difficulties which might occur in the case of a mixing of the coolant with the reaction mixture.

Among the difficulties which are to be precluded according to the invention are, one the one hand, the undesired heating of the mixture arising by reaction between the components of the reaction mixture and those of the coolant, the formation of highly corrosive mixtures, and the evolution of poisonous gases or vapors. One the other hand, the need to dispose of the resulting mixture can also create difficulties. From these points of view, water would be an unsuitable coolant because it forms a highly corrosive mixture. Aqueous alkalies, too, are unusable because they would react with hydrogen fluoride with strong evolution of heat.

It has now been found that the aforementioned problem can be solved if the reaction mixture is maintained at a constant reaction temperature in a heat exchanger using an addition product of at least two of the aforementioned starting materials as the coolant. The invention also covers the case where one or more of the aforementioned addition products itself is used as a starting material in the manufacture of isobutyric acid.

In case of a leak, no materials from the cooling system will reach the reaction mixture which are not already present there or which would not react in the same way as the components of the reaction mixture. Preferably, the pressure of the coolant is below that of the reaction mixture so that, in case of a leak, part of the reaction mixture would penetrate into the cooling system. In this way, the corrosiveness of the mixture is, to be sure, altered and a contamination arises which is tolerable for only the short time required to eliminate the leak. Nevertheless, no direct damages result. Above all, the contaminated coolant is not lost and need not be disposed of, but rather can be stored temporarily in a container and used as starting material for the manufacture of isobutyric acid or its derivatives. Preferably, such usage would be within limited amounts, for example 1 to 10% of the conventional starting material.

Practice of the Invention

Various binary or ternary addition products form between the starting materials which are used as reagents or as catalyst in the Koch synthesis of isobutyric acid, namely:

a) isopropyl fluoride from propylene and hydrogen fluoride;

b) isopropanol and diisopropylether from propylene and water;

c) Methyl isopropyl ether from propylene and methanol;

d) formic acid from carbon monoxide and water;

e) methyl formate from carbon monoxide and methanol;

f) formic acid fluoride from carbon monoxide and hydrogen fluoride; and g) isopropyl formate from propylene, carbon monoxide, and water.

The coolant is so chosen from among these possible addition products such that it undergoes no noticeable decomposition in the temperature range in which it is used. Preferably an addition product with a boiling point above 70° C. (at normal pressure) is used. From the point of view of its stability at high temperature, its slight corrosiveness, and its relatively low vapor pressure at the operating temperature, isopropanol is the most suitable coolant in most cases. For the preparation of isobutyric acid fluoride, isopropyl fluoride is preferred as a coolant. For the manufacture of isobutyric acid methyl ester, methyl isopropyl ether is usable.

The wall of the reactor in which the reaction occurs can serve as the heat exchanger if it is surrounded in a known fashion with a cooling mantle through which the coolant flows. A tube-bundle heat exchanger can also be used, which is dipped into the reaction mixture or through which the reaction mixture flows in countercurrent.

In contact with the hot reactor wall, the coolant is heated to a temperature which can be close to the temperature of the reaction mixture, but which as a rule is 5° K to 20° K lower. Preferably isopropanol is warmed to a maximum of 140° C. If the cooling system is arranged to effect heat exchange between two fluid media, it may be necessary to operate the cooling system under pressure, for example up to 10 bars, to avoid heating the coolant above its boiling point. However, as already mentioned, the pressure of the reaction mixture is not exceeded if possible.

In order to make the extracted heat useful somewhere else, the cooling system can be kept under a pressure at which the coolant vaporizes during the heat exchange, for example 0.1 to 10 bars; the latent heat absorbed up can be recovered on condensation.

The coolant is suitably moved in a closed circulation by means of a circulation pump. The coolant is lead from the heat exchange surfaces of the reactor into a cooler where it is cooled to a lower temperature or is condensed by means of a cooler liquid or gaseous medium, e.g. cooling water or air. The heat can also be used to preheat the starting materials of a processing medium of a related method. The coolant is returned from the cooler to the heat exchanger of the reactor at a temperature below the reaction temperature.

It is advantageous to keep the cooling system, and particularly the volume of the coolant therein, as small as possible so that in case of a leak not too large amounts of contaminated coolant need be stored for later use.

What is claimed is:

1. A method for reacting about stoichiometric amounts of propylene, carbon monoxide, and water or alcohol, respectively, in the Koch synthesis in liquid hydrogen fluoride as a Koch catalyst, to form isobutyric acid or an ester thereof, respectively, which method comprises keeping the reaction mixture at a constant reaction temperature by passing it through a heat exchanger employing an addition product of two of the aforementioned materials as a coolant, conducting said coolant from said heat exchanger to a cooler where it is cooled to a temperature below the reaction temperature, and then returning said coolant from said cooler to said heat exchanger in closed circulation.

2. A method as in claim 1 wherein said addition product has a normal boiling point above 70° C.

3. A method as in claim 1 wherein said coolant is under a pressure at which it vaporizes in the heat exchanger.

4. A method as in claim 3 wherein said coolant is isopropanol.

5. A method for reacting about stoichiometric amounts of propylene and carbon monoxide in the Koch synthesis in liquid hydrogen fluoride as a Koch catalyst to form isobutyric acid fluoride, which method comprises keeping the reaction mixture at a constant reaction temperature by passing it through a heat exchanger employing an addition product of two of the aforementioned materials as a coolant, conducting said coolant from said heat exchanger to a cooler where it is cooled to a temperature below the reaction temperature, and then returning said coolant from said cooler to said heat exchanger in closed circulation.

6. A method as in claim 5 wherein said coolant is under a lower pressure than the reaction mixture.

7. A method as in claim 5 wherein said addition product has a normal boiling point above 70° C.

* * * * *